United States Patent [19]

Tanouchi et al.

[11] 4,374,845
[45] Feb. 22, 1983

[54] 1-(7-CARBOXY-2-OCTYNYL)IMIDAZOLE DERIVATIVES, PHARMACEUTICAL COMPOSITIONS AND USE

[75] Inventors: Tadao Tanouchi, Takatsuki; Masanori Kawamura, Ibaraki; Masaki Hayashi, Takatsuki, all of Japan

[73] Assignees: Kissei Pharmaceutical Co., Osaka; Ono Pharmaceutical Co., Ltd., Nagano, both of Japan

[21] Appl. No.: 313,847

[22] Filed: Oct. 22, 1981

[30] Foreign Application Priority Data

Oct. 22, 1980 [JP] Japan ................................ 55-146837

[51] Int. Cl.³ .................. A61K 31/415; C07D 233/60
[52] U.S. Cl. ................................. 424/273 R; 548/341
[58] Field of Search ..................... 548/341; 424/273 R

[56] References Cited

U.S. PATENT DOCUMENTS 4,256,757 3/1981 Hayashi et al. ..................... 548/341

Primary Examiner—Robert W. Ramsuer
Attorney, Agent, or Firm—Sughrue, Mion, Zinn, Macpeak & Seas

[57] ABSTRACT

The imidazole derivatives of the general formula:

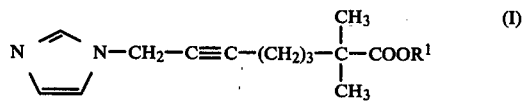

(wherein $R^1$ represents a hydrogen atom or straight- or branched-chain alkyl group of 1 to 4 carbon atoms), or pharmaceutically acceptable non-toxic salts thereof, which have a specifically inhibitory effect on the biosynthesis of thromboxane $A_2$ (abbreviated as $TXA_2$ hereafter) and are, therefore, useful as treating agents for disease caused by $TXA_2$ such as inflammation, cerebral apoplexy, miocardial infarction, acute cardiac death, cardiostenosis and thrombus etc.

8 Claims, No Drawings

1-(7-CARBOXY-2-OCTYNYL)IMIDAZOLE DERIVATIVES, PHARMACEUTICAL COMPOSITIONS AND USE

The present invention is concerned with new imidazole derivatives and pharmaceutical compositions containing them.

Up to now, as compounds having an inhibitory activity on the biosynthesis of thromboxane $A_2$ (abbreviated $TXA_2$ hereafter), (i) sodium p-benzyl-4-[1-oxo-2-(4-chlorobenzyl)-3-phenylpropyl]-phenylphosphonate (N-0164), (ii) 2-isopropyl-3-nicotinylindole (L-8027), (iii) 9,11-epoxymethanoprostanoic acid and (iv) imidazole etc. [cf. Annual Review of Biochemistry 47, 1002-1004 (1978)] have been known.

Furthermore, it has been recently found that imidazole derivatives having various substituents at the 1-position thereof, possess a strong inhibitory effect on the biosynthesis of $TXA_2$. (cf. our British Patent Publication Nos. 2016452A, 2024807A, 2025946A and 2031408A).

The present inventors have conducted extensive investigations in order to discover a new imidazole derivative which strongly inhibits the biosynthesis of $TXA_2$, and have found that the imidazole derivatives of the present invention achieve the objects and thus completed the present invention.

Accordingly, the present invention provides new imidazole derivatives of the general formula:

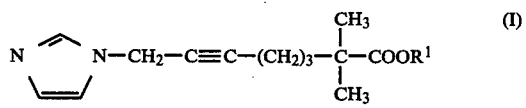

(wherein $R^1$ represents a hydrogen atom or straight- or branched-chain alkyl group of 1 to 4 carbon atoms), or pharmaceutically acceptable non-toxic salts thereof, which have a specifically inhibitory effect on the biosynthesis of thromboxane $A_2$ (Abbreviated as $TXA_2$ hereinafter) and are, therefore, useful as treating agents for disease caused by $TXA_2$, such as inflammation, cerebral apoplexy, myocardial infarction, acute cardiac death, cardiostenosis and thrombus etc.

Examples of the straight- or branched-chain alkyl group of 1 to 4 carbon atoms represented by $R^1$ in general formula (I) are methyl, ethyl, propyl and butyl group and isomers thereof. Preferably $R^1$ represents a hydrogen atom, methyl group or ethyl group.

According to a feature of the present invention, compounds of general formula (I) wherein $R^1$ represents a straight- or branched-chain alkyl group of 1 to 4 carbon atoms, i.e. compounds of the general formula:

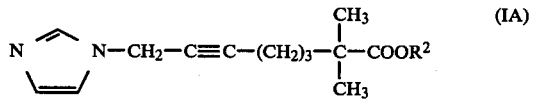

(wherein $R^2$ represents a straight- or branched-chain alkyl group of 1 to 4 carbon atoms) may be prepared by reacting a metal salt, e.g. silver salt or alkali metal salt such as sodium salt, of imidazole with a halogen compound of the general formula:

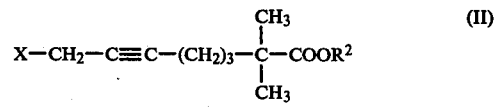

(wherein X represents a halogen atom and $R^2$ is as hereinbefore defined).

As reaction solvent used in the above reaction, there may be used any one of that does not influence the reaction, and usually benzene, toluene, xylene, N,N-dimethylformamide, acetonitrile or a lower alkanol etc. The reaction may be carried out at a temperature from 0° C. to 150° C., usually from room temperature to a reflux temperature of reaction solvents.

Compounds of general formula (I) wherein $R^1$ represents a hydrogen atom, i.e. the compound of the formula:

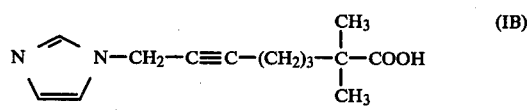

may be prepared by hydrolysing compounds of general formula (IA) under alkaline conditions.

The hydrolysis may be carried out in an aqueous solution of a hydroxide or carbonate of alkali metal such as sodium or potassium in the presence or in the absence of a water-miscible solvent, e.g. an ether such as tetrahydrofuran or a lower alkanol such as methanol or ethanol. Compounds of general formula (I) are purified by conventional methods, for example, distillation under normal or reduced pressure, or high speed liquid chromatography, thin layer chromatography or column chromatography on silica gel or recrystallization etc.

Metal salts of imidazole may be prepared by reacting an imidazole with an alkali metal hydride such as sodium hydride, an alkali metal alcoholate such as sodium methoxide, an alkali metal carbonate such as sodium or potassium carbonate, an alkali metal hydroxide such as sodium or potassium hydroxide or a silver oxide in an inert solvent. These metal salts may be used as isolated compounds or as a solution of the salts.

Halogen compounds of general formula (II) may be prepared by the series reactions depicted schematically below.

SCHEME

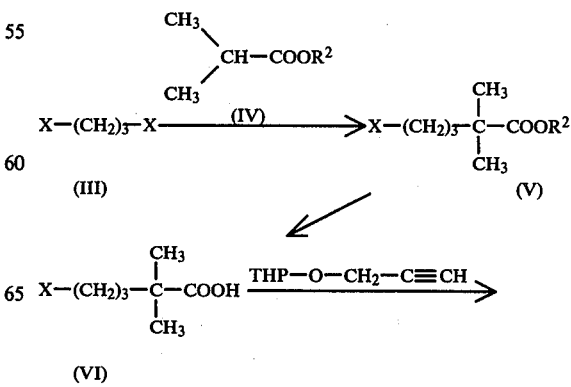

-continued $$THP-O-CH_2-C\equiv C-(CH_2)_3-\underset{\underset{CH_3}{|}}{\overset{\overset{CH_3}{|}}{C}}-COOH$$

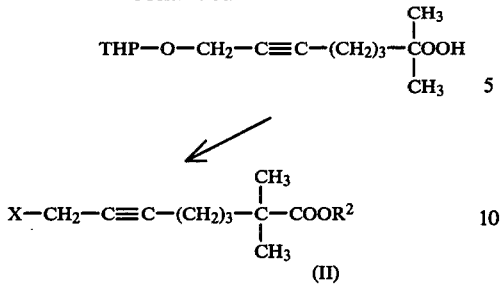

$$X-CH_2-C\equiv C-(CH_2)_3-\underset{\underset{CH_3}{|}}{\overset{\overset{CH_3}{|}}{C}}-COOR^2$$

(II)

wherein, THP represents a tetrahydropyran-2-yl group, and X and $R^2$ represent as hereinbefore defined.

Compounds of general formula (V) may be prepared by reacting compounds of general formula (IV) using a lithioating agent such as butyl lithium or lithium diisopropylamide, to obtain a lithium compound and reacting the resulting compound with 1,3-dihalopropane of the general formula (III).

The above reaction may be effected in an inert organic solvent such as tetrahydrofuran, diethyl ether, hexane or hexamethylphosphamide (HMPA) or the mixture of them at a low temperature from $-78°$ C. to room temperature. Compounds of general formula (VI) may be prepared by hydrolysing compounds of general formula (V). The hydrolysis may be effected using boron trichloride so that by-products can not be produced by reacting the halogen moiety of compounds of general formula (V).

2,2-Dimethyl-8-(tetrahydropyran-2-yloxy)-6-octynoic acid may be prepared from 3-(tetrahydropyran-2-yloxy)-1-propyne and compounds of general formula (VI), by means heretofore mentioned for the preparation of compounds of general formula (V) from compounds of general formula (IV) and (III).

The octynoic acid thus obtained may be esterified, for example by using a diazoalkane, and then halogenated with a halogenated agent such as halogenated phosphorus to obtain compounds of general formula (II).

Acid addition salts of imidazole derivatives of general formula (I) may be prepared from the compounds of general formula (I) by methods known per se, for example, by reaction of stoichiometric quantities of a compound of general formula (I) and an appropriate acid, e.g. an inorganic acid such as hydrochloric acid, hydrobromic acid, hydroiodic acid, sulphuric acid, phosphoric acid or nitric acid, or an organic acid such as acetic acid, lactic acid, tartaric acid, benzoic acid, citric acid, methanesulphonic acid, ethanesulphonic acid, benzenesulphonic acid, toluenesulphonic acid or isethionic acid, in a suitable solvent.

Neutral salts may be prepared from the acids of general formula (I) wherein $R^1$ represents a hydrogen atom, by methods known per se, for example, by reaction of stoichiometric quantities of an acid of general formula (I) and an appropriate base, e.g. an alkali metal or alkaline earth metal hydroxide or carbonate, or an organic amine, in a suitable solvent.

Preferably acid addition salts and neutral salts are non-toxic salts. By the term 'non-toxic salts' as used in this specification, is meant salts the anions or cations of which are relatively innocuous to the animal organism when used in therapeutic doses so that the beneficial pharmacological properties of the compounds of general formula (I) are not vitiated by side effects ascriable to those anions or cations. Preferably the salts are water-soluble. Suitable acid addition salts of imidazole derivatives are, for example, inorganic acid salts such as hydrochloride, hydrobromide, hydroiodide, sulfate, phosphate, nitrate, or organic acid salts such as acetate, lactate, tartrate, benzoate, citrate, methanesulphonate, ethanesulphonate, benzenesulphonate, toluenesulphonate or isethionate. Suitable neutral salts include the alkali metal, e.g. sodium or potassium salts, the alkaline earth metal, e.g. calcium or magnesium salts and ammonium salts, and pharmaceutically acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups of 1 to 6 carbon atoms and hydroxyalkyl groups of 1 to 3 carbon atoms. Suitable nontoxic amine salts are, e.g. tetraalkylammonium salts such as tetramethylammonium salts, and the other organic amine salts such as methylamine salts, dimethylamine salts, cyclopentylamine salts, benzylamine salts, phenetylamine salts, piperidine salts, monoethanolamine salts, diethanolamine salts, lysine salts and arginine salts.

The imidazole derivatives of general formula (I) and non-toxic salts thereof possess an inhibitory effect on the biosynthesis of $TXA_2$, and are, therefore, useful for controlling the biosynthesis of $TXA_2$ in mammals including humans when it is desired.

For example, in standard laboratory tests, 1-(7-carboxy-7-methyl-2-octynyl)imidazole hydrochloride produce a 50% inhibition of thromboxane synthetase from rabbit platelet microsomes at the molar concentrations of $9\times 10^{-9}$.

To control the biosynthesis of $TXA_2$ is useful for the prevention and treatment of inflammation, cerebral apoplexy, myocardial infarction, acute cardiac death, cartiostenosis and thrombus in mammals including humans, especially in humans. For such purpose, the compounds of the present invention are usually administered systemically, for example, orally, rectally or parenterally.

Doses are determined depending upon age, symptoms, the desired therapeutic effect, the route of administration, the duration of the treatment and the like, and are generally and preferably about 10 mg to 1 g for oral administration, and 0.01 mg to 10 mg for intravenous injection or 1 μg to 100 μg/hour for continuous intravenous infusion, specially when required emergency treatment.

It was confirmed that the value of $LD_{50}$ is more than 5,000 mg/kg by oral administration to rats concerning to the toxicity of compounds of the present invention and therefore, these compounds are considered to be usable enough as pharmaceuticals.

Solid compositions for oral administration include compressed tablets, pills, dispersible powders and granules. In such solid compositions, one or more of the active compounds is or are, admixed with at least one inert diluent such as calcium carbonate, potato starch, alginic acid or lactose. The compositions may also comprise, as is normal practice, additional substances other than inert diluents, e.g. lubricating agents such as magnesium stearate. Liquid compositions for oral administration include pharmaceutically acceptable emulsions, solutions, suspentions, syrups and elixirs containing inert diluents commonly used in the art, such as water or liquid paraffin. Besides inert diluents such compositions may also comprise adjuvants such as wetting and suspending agents, and sweetening, flavouring, perfuming and preservating agents. The compositions according to the invention for oral administration, also include capsules of absorbable materials such as containing one or more of the active substances with or without the addition of diluents or excipients.

Solid compositions for intrarectal administration include suppositories formulated in manner known per se and containing one or more of the active compounds.

Preparation according to invention for parenteral administration include sterile aqueous of non-aqueous solutions, suspensions or emulsions. Example of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may also be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

The following Reference Examples and Examples illustrate, but not limit, the preparation of compounds of the present invention. In the Reference Examples and Examples, 'TLC', 'IR', 'NMR', 'MS' represent respectively. 'Thin layer chromatography', 'Infrared absorption spectrum', 'Nuclear magnetic resonance spectrum' and 'Mass spectrum'. Where solvent ratios are specified in chromatographic separations, the ratios are by volume: the solvents in parentheses in thin layer chromatography show the developing solvent used. Except when specified otherwise, infrared spectra are recorded by the liquid film method, and nuclear magnetic resonance spectra are recorded in deuterochloroform ($CDCl_3$) solutions.

REFERENCE EXAMPLE 1

Ethyl 2,2-dimethyl-5-bromopentanoate

To 5.05 g of diisopropylamine in 100 ml of anhydrous tetrahydrofuran was added dropwise 35.6 ml of n-butyl lithium (1.4 M solution in hexane) at −70° C., the mixture was stirred at the same temperature for 15 minutes, and added dropwise 6.1 g of ethyl isobutylate in 30 ml of anhydrous tetrahydrofuran and the mixture was stirred for 30 minutes. To the solution was added dropwise 15.2 ml of 1,3-dibromopropane at −70° C., and the mixture was stirred for 5 minutes, and 13.5 g of hexamethylphosphamide, and the temperature of the mixture was raised slowly from −70° C. to room temperature with stirring for one hour. The reaction solution was concentrated and the residue was added 50 ml of a 1 N solution of hydrochloric acid and the mixture was extracted with diethyl ether. The extract was washed with a 1 N solution of hydrochloric acid, an aqueous saturated solution of sodium hydrocarbonate and a saturated solution of sodium chloride, and dried over anhydrous magnesium sulfate, and concentrated under reduced pressure. The residue was purified by column chromatography on silica gel using a mixture of methylene chloride and cyclohexane (2:1) as an eluent to give 10.1 g of the title compound having the following physical characteristic:
TLC (benzene): Rf=0.50.

REFERENCE EXAMPLE 2

2,2-dimethyl-5-bromopentanoic acid

To 7.1 g of the ester (prepared in Reference Example 1) in 70 ml of anhydrous methylene chloride was added dropwise 71 ml of a 20% solution boron trichloride in methylene chloride at −25° C., and the mixture was stirred at 0° C. for one hour and at room temperature for 5 hours, and poured into ice-water, and the mixture was extracted with chloroform. The extract was washed with water and a saturated solution of sodium chloride, and dried over anhydrous magnesium sulfate, and concentrated under reduced pressure. The residue was purified by column chromatography on silica gel using a mixture of ethyl acetate and cyclohexane (2:1) as an eluent to give 4.9 g of the title compound having the following physical characteristic:
TLC (benzene:ethylene acetate=2:1): RF=0.50.

REFERENCE EXAMPLE 3

2,2-dimethyl-8-(tetrahydropyran-2-yloxy)-6-octynoic acid

To 8.15 g of 3-(tetrahydropyran-2-yloxy)-1-propyne in 120 ml of anhydrous tetrahydrofuran was added 20.3 ml of hexamethylphosphamide, and the mixture was added dropwise 41.3 ml of n-butyl lithium (1.4 M solution in hexane) at −70° C., and stirred at the same temperature for 30 minutes, the mixture was added 4.85 g of pentanoic acid (prepared in Reference Example 2) in 30 ml of anhydrous tetrahydrofuran, the mixture was stirred at room temperature for 3 hours, and cooled to 0° C., and added an aqueous saturated solution of ammonium chloride for stopping the reaction. The reaction mixture was concentrated under reduced pressure. The residue was added to 100 ml of a 1 N solution of hydrochloric acid, and the mixture was extracted with diethyl ether. The extract was washed with an aqueous saturated solution of sodium chloride, and dried over anhydrous magnesium sulfate, and concentrated under reduced pressure. The residue was purified by column chromatography on silica gel using a mixture of methylene chloride and cyclohexane (7:3) as an eluent to give 1.69 g of the title compound having the following physical characteristic:
TLC (benzene:ethyl acetate=2:1): RF=0.50.

REFERENCE EXAMPLE 4

1-bromo-7-methoxycarbonyl-7-methyl-2-octyne

To 300 mg of octynoic acid (prepared in Reference Example 3) in 3.4 ml of diethyl ether was added a solution of diazomethane in diethyl ether at 0° C., and the mixture was stirred for 30 minutes, and concentrated under reduced pressure. To a solution of 300 mg of the residue dissolved in 1 ml of diethyl ether, was added 42 μl of phosphorus trichloride at 20° C., the mixture was stirred at room temperature for 2 hours, and added 30 ml of diethyl ether, and the mixture was washed with water and an aqueous saturated solution of sodium chloride, successively, and dried over anhydrous magnesium sulfate, and concentrated under reduced pressure. The residue was purified by column chromatography on silica gel using a mixture of chloroform and cyclohexane (2:1) as an eluent to give 115 mg of the title compound having the following physical characteristic:

TLC (methylene chloride: RF=0.85.

EXAMPLE 1

1-(7-methoxycarbonyl-7-methyl-2-octynyl)imidazole

To 290 mg of the bromide (prepared in Reference Example 4) in 3.4 ml of toluene was added 392 mg of imidazole silver salt (prepared as described in Example 3 of our U.S. Pat. No. 4,256,757 or in Example 3 of our British Patent Publication No. 2024807A), and the mixture was refluxed for one hour. The reaction mixture was filtered, and the filtrate was concentrated under reduced pressure. The residue was purified by column chromatography on silica gel using a mixture of chloroform and methanol (100:3) as an eluent to give 169 mg of the title compound having the following physical characteristics:

TLC (chloroform:methanol=9:1): RF=0.40;

IR: $\nu$=1738, 1510, 1480, 1400, 1283, 1240, 1207, 1140 cm$^{-1}$;

NMR: $\delta$=7.50 (1H, S), 6.95 (2H, S), 4.62 (2H, t), 3.56 (3H, S), 2.45−2.00 (2H, m), 1.87−1.33 (4H, m), 1.18 (6H, S);

MS (%): m/e=249 (M$^+$+1, 18), 248 (M$^+$, 90), 199 (40), 148 (25), 133 (40), 121 (25), 120 (25), 119 (33), 102 (38), 93 (22), 86 (45), 84 (75), 79 (40), 69 (100).

EXAMPLE 2

1-(7-carboxy-7-methyl-2-octynyl)imidazole hydrochloride

To 169 mg of the ester comound (prepared in Example 1) was added 1.3 ml of a 2 N solution of sodium hydroxide and 2 ml of methanol, and the mixture was refluxed for 20 hours, and then concentrated, and the residue was washed with diethyl ether, and adjusted to pH 2 with a 2 N solution of hydrochloric acid, the solution was evaporated to dryness under reduced pressure. To the residue was added ethanol to dissolve, and the insoluble material was removed off. To the filtrate was added diethyl ether to deposit crystals and 129 mg of the title compound having the following physical characteristics was obtained.

Melting point: 111°-114° C.;

IR (KBr tablet): $\nu$=3420, 3140, 3020, 1726, 1562, 1171, 1133, 1072, 768, 628 cm$^{-1}$;

NMR (D$_2$O solution): $\delta$=8.88 (1H, b-s), 7.65 (1H, b-s), 7.55 (1H, b-s), 5.10 (2H, t), 2.33 (2H, m) 1.61 (4H, m), 1.18 (6H, s);

MS (%): m/e=234 (M$^+$, 1.7), 189 (7), 175 (6), 133 (10), 119 (13), 107 (11), 93 (12), 85 (20), 81 (13).

EXAMPLE 3

10 g of 1-(7-carboxy-7-methyl-2-octynyl)imidazole hydrochloride, 200 mg of cellulose calcium gluconate (disintegrator), 100 mg of magnesium stearate (lubricating agent) and 9.7 g of crystal cellulose were mixed and punched out in a conventional manner to obtain tablets each containing 100 mg of the active ingredient.

We claim:

1. Imidazole derivatives of the general formula:

$$\text{N}\overset{\frown}{\underset{\smile}{\phantom{N}}}\text{N}-\text{CH}_2-\text{C}\equiv\text{C}-(\text{CH}_2)_3-\underset{\underset{\text{CH}_3}{|}}{\overset{\overset{\text{CH}_3}{|}}{\text{C}}}-\text{COOR}^1 \quad (I)$$

(wherein R$^1$ represents a hydrogen atom, or straight- or branched-chain alkyl group of 1 to 4 carbon atoms), or pharmaceutically acceptable non-toxic salts thereof.

2. Compounds according to claim 1 wherein R$^1$ represents a hydrogen atom, a methyl group or an ethyl group.

3. Compounds according to claim 1 wherein R$^1$ represents a hydrogen atom.

4. A compound according to claim 1 which is 1-(7-methoxycarbonyl-7-methyl-2-octynyl)imidazole.

5. A compound according to claim 1 which is 1-(7-carboxy-7-methyl-2-octynyl)imidazole or its hydrochloride.

6. Pharmaceutically acceptable non-toxic salts of imidazole derivatives according to claim 1.

7. Pharmaceutical compositions which comprise, as active ingredient, in an amount sufficient to inhibit biosynthesis of thromboxane A$_2$, at least one compound of general formula (I) depicted in claim 1, wherein various symbols are as defined in claim 1, or pharmaceutically acceptable non-toxic salt thereof, together with a pharmaceutical carrier or coating.

8. A method for inhibiting the biosynthesis of thromboxane A$_2$ which comprise the administration of an effective amount of a compound as claimed in claim 1 or pharmaceutically acceptable non-toxic salt thereof.

* * * * *